US011364123B2

(12) United States Patent
Tong et al.

(10) Patent No.: US 11,364,123 B2
(45) Date of Patent: Jun. 21, 2022

(54) THREE-DIMENSIONAL POROUS STRUCTURES FOR BONE INGROWTH AND METHODS FOR PRODUCING

(71) Applicant: DePuy Ireland Unlimited Company, Ringaskiddy (IE)

(72) Inventors: Weidong Tong, Warsaw, IN (US); Andrew T. Rosenberger, Warsaw, IN (US); Robert J. Kane, Warsaw, IN (US); Bryan J. Smith, Warsaw, IN (US); Luke C. Ice, Warsaw, IN (US); Fionnán Aodhán McNamara, Ringaskiddy (IE); Edward Patrick Kavanagh, Ringaskiddy (IE)

(73) Assignee: DePuy Ireland Unlimited Company

( * ) Notice: Subject to any disclaimer, the term of this patent is extended or adjusted under 35 U.S.C. 154(b) by 222 days.

(21) Appl. No.: 16/365,557

(22) Filed: Mar. 26, 2019

(65) Prior Publication Data
US 2019/0290441 A1  Sep. 26, 2019

Related U.S. Application Data

(60) Provisional application No. 62/648,353, filed on Mar. 26, 2018.

(51) Int. Cl.
*A61F 2/28* (2006.01)
*A61F 2/30* (2006.01)
*A61F 2/38* (2006.01)

(52) U.S. Cl.
CPC ............ *A61F 2/30771* (2013.01); *A61F 2/28* (2013.01); *A61F 2/30767* (2013.01);
(Continued)

(58) Field of Classification Search
CPC .... A61F 2002/3028; A61F 2002/30911; A61F 2002/30912; A61F 2002/30914; A61F 2002/30915; A61F 2002/30769
See application file for complete search history.

(56) References Cited

U.S. PATENT DOCUMENTS 4,038,703 A  8/1977 Bokros
4,479,271 A  10/1984 Bolesky et al.
(Continued)

FOREIGN PATENT DOCUMENTS

EP  1800700 A2  6/2007
EP  2319462 A1  5/2011
(Continued)

OTHER PUBLICATIONS

Bobyn et al, Characteristics of bone ingrowth and interface mechanics of a new porous tantalum biomaterial; The Journal of Bone & Joint Surgery, vol. 81-B, No. 5, Sep. 1999, 907-914.
(Continued)

*Primary Examiner* — Megan Y Wolf
(74) *Attorney, Agent, or Firm* — BakerHostetler

(57) ABSTRACT

An orthopaedic prosthetic component is provided. The orthopaedic prosthetic component comprises a porous three-dimensional structure shaped to be implanted in a patient's body. The porous three-dimensional structure comprises a plurality of unit cells. At least one unit cell comprises a first geometric structure having a first geometry and comprising a plurality of first struts, and a second geometric structure having a second geometry and comprising a plurality of second struts connected to a number of the plurality of first struts to form the second geometric structure.

15 Claims, 6 Drawing Sheets

(52) U.S. Cl.
CPC ..... *A61F 2/389* (2013.01); *A61F 2002/30011* (2013.01); *A61F 2002/3028* (2013.01); *A61F 2002/3092* (2013.01); *A61F 2002/3093* (2013.01); *A61F 2002/30593* (2013.01); *A61F 2002/30769* (2013.01); *A61F 2002/30777* (2013.01); *A61F 2002/30787* (2013.01); *A61F 2002/30878* (2013.01); *A61F 2002/30971* (2013.01)

(56) References Cited

U.S. PATENT DOCUMENTS

| | | | |
|---|---|---|---|
| 4,795,472 | A | 1/1989 | Crowninshield et al. |
| 4,842,517 | A | 6/1989 | Kawahara et al. |
| 4,938,769 | A | 7/1990 | Shaw |
| 4,997,445 | A | 3/1991 | Hodorek |
| 5,387,243 | A | 2/1995 | Devanathan |
| 5,534,030 | A | 7/1996 | Navarro et al. |
| 5,534,032 | A | 7/1996 | Hodorek |
| 5,609,641 | A | 3/1997 | Johnson et al. |
| 5,702,484 | A | 12/1997 | Goymann et al. |
| 5,716,358 | A | 2/1998 | Ochoa et al. |
| 5,723,011 | A | 3/1998 | Devanathan et al. |
| 6,027,682 | A | 2/2000 | Almquist et al. |
| 6,080,219 | A | 6/2000 | Jha et al. |
| 6,869,448 | B2 | 3/2005 | Tuke et al. |
| 7,537,664 | B2 | 5/2009 | O'Neill et al. |
| 7,597,715 | B2 | 10/2009 | Brown et al. |
| 8,021,432 | B2 | 9/2011 | Meridew et al. |
| 8,266,780 | B2 | 9/2012 | Bollinger et al. |
| 8,268,099 | B2 | 9/2012 | O'Neill et al. |
| 8,268,100 | B2 | 9/2012 | O'Neill et al. |
| 8,470,047 | B2 | 6/2013 | Hazebrouck et al. |
| 8,556,981 | B2 | 10/2013 | Jones et al. |
| 8,562,348 | B2 | 10/2013 | Collins et al. |
| 8,590,157 | B2 | 11/2013 | Kruth et al. |
| 8,888,862 | B2 | 11/2014 | McDonnell et al. |
| 8,992,703 | B2 | 3/2015 | O'Neill et al. |
| 9,180,010 | B2 | 11/2015 | Dong et al. |
| 9,456,901 | B2 | 10/2016 | Jones et al. |
| 10,307,260 | B2 | 6/2019 | Heldreth et al. |
| 10,399,147 | B2 | 9/2019 | Scott et al. |
| 2002/0120344 | A1 | 8/2002 | Meulink et al. |
| 2003/0180171 | A1 | 9/2003 | Artz et al. |
| 2004/0236430 | A1 | 11/2004 | Koch et al. |
| 2009/0216325 | A1 | 8/2009 | May et al. |
| 2010/0298947 | A1 | 11/2010 | Unger |
| 2012/0321878 | A1* | 12/2012 | Landon ............... A61L 27/56 428/304.4 |
| 2013/0172927 | A1 | 7/2013 | Natarajan et al. |
| 2013/0218284 | A1 | 8/2013 | Eickmann et al. |
| 2013/0325129 | A1 | 12/2013 | Huang |
| 2014/0257507 | A1 | 9/2014 | Wang et al. |
| 2017/0095337 | A1 | 4/2017 | Pasini et al. |
| 2017/0266007 | A1 | 9/2017 | Gelaude et al. |
| 2018/0228613 | A1* | 8/2018 | Jones ..................... A61F 2/44 |
| 2019/0046322 | A1 | 2/2019 | Theken et al. |
| 2019/0151113 | A1 | 5/2019 | Sack |
| 2019/0298525 | A1 | 10/2019 | Wright et al. |
| 2019/0298533 | A1 | 10/2019 | Kane |
| 2020/0036011 | A1 | 1/2020 | Numata et al. |
| 2020/0129670 | A1 | 4/2020 | Landon et al. |
| 2021/0085466 | A1 | 3/2021 | Tong |

FOREIGN PATENT DOCUMENTS

| | | |
|---|---|---|
| EP | 2774580 | 9/2014 |
| JP | 2002-038201 A | 2/2002 |
| WO | 96/23459 A1 | 8/1996 |
| WO | 2009/022911 A2 | 2/2009 |

OTHER PUBLICATIONS

Chua et al, Development of a Tissue Engineering Scaffold Structure Library for Rapid Prototyping. Part 1: Investigation and Classification, Int J Adv Manuf Technol, 2003, 21:291-301.

Chua et al, Development of a Tissue Engineering Scaffold Structure Library for Rapid Prototyping. Part 2: Parametric Library and Assembly Program, Int J Adv Manuf Technol, 2003, 21: 302-312.

Hong et al, A New Ti-5Ag Alloy for Customized Prostheses by Three-dimensional Printing (3DPtm), Research Reports, Biomaterials & Bioengineering, J Dent Res 80(3), 2001, 860-863.

Meiners et al, Direct Generation of Metal Parts and Tools by Selective Laser Powder Remelting (SLPR); Fraunhofer Institute for Laser Technology (ILT), 1999, 655-662.

Morgan et al, Direct Metal Laser Re-Melting (DMLR) of 316L Stainless Steel Powder, Part 1: Analysis of Thin Wall Structures, Research in Advanced Technologies Group, Faculty of Engineering, The University of Liverpool, UK, 2001, 276-282.

Morgan et al, Direct Metal Laser Re-Melting of 316L Stainless Steel Powder, Part 2: Analysis of Cubic Primitives, Research in Advanced Technologies Group, Faculty of Engineering, The University of Liverpool, UK, 2001, 283-295.

Morgan et al, Experimental investigation of nanosecond pulsed Nd:YAG laser re-melted pre-placed powder beds, Rapid Prototyping Journal, vol. 7, No. 3, 2001, 159-172.

Morgan et al, High density net shape components by direct laser re-melting of single-phase powders, Journal of Materials Science 37 (2002), 3093-3100.

Mullen et al, Selective Laster Melting: A Unit Cell Approach for the Manufacture of Porous, Titanium, Bone In-Growth Constructs, Suitable for Orthopedic Applications. II. Randomized Structures, Journal of Biomedical Materials Research Part B: Applied Biomaterials, Jan. 2010, 178-188.

Pogson et al, The production of copper parts using DMLR, Rapid Prototyping Journal, vol. 9, No. 5, 2003, 334-343.

Ramos et al, Mechanics of the Selective Laser Raster-Scanning Surface Interaction, Department of Mechanical and Metallurgical Engineering, Pontificia Universidad, Chile, Department of Mechanical Engineering, University of Texas at Austin, Aug. 2003, 559-572.

Williams et al, Selective Laser Sintering Part Strength as a Function of Andrew Number, Scan Rate and Spot Size, Clemson University, 1996, 10 pages.

Williams, et al, Advances in modeling the effects of selected parameters on the SLS process, Rapid Prototyping Journal, vol. 4, No. 2, 1998, 90-100.

Wysocki et al, Laser and Electron Beam Additive Manufacturing Methods of Fabricating Titanium Bone Implants, Applied Sciences, 7, 657, 2017, 20 pages.

Yang et al, the design of scaffolds for use in tissue engineering, Part II. Rapid prototyping techniques, Tissue engineering, Feb. 2002; vol. 8(1), 1-11.

Yang et al, The design of scaffolds for use in tissue engineering. Part I. Traditional factors, Tissue engineering, Dec. 2001; vol. 7(6), 679-689.

Non-Final Rejection dated Jan. 20, 2022 in U.S. Appl No. 17/028,022, filed Sep. 22, 2020, 14 pages.

* cited by examiner

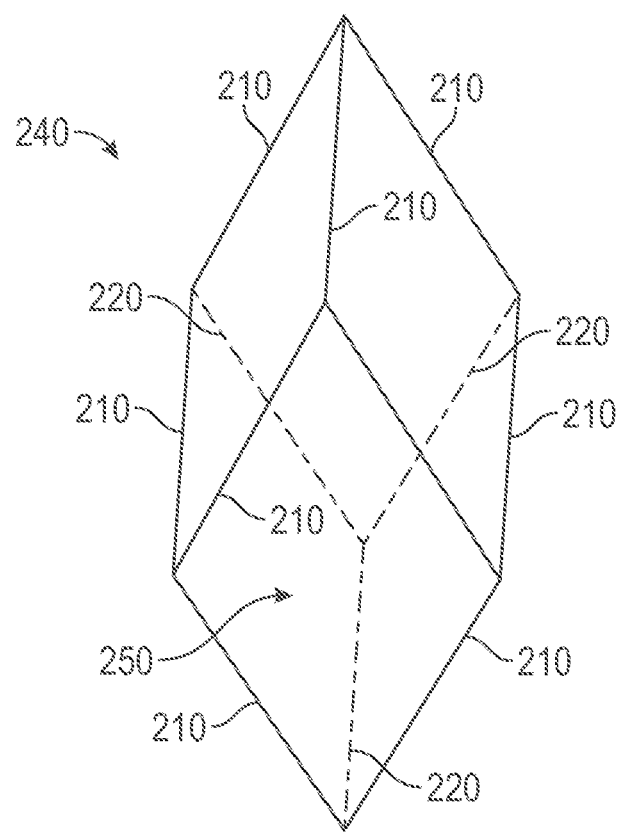
FIG. 5
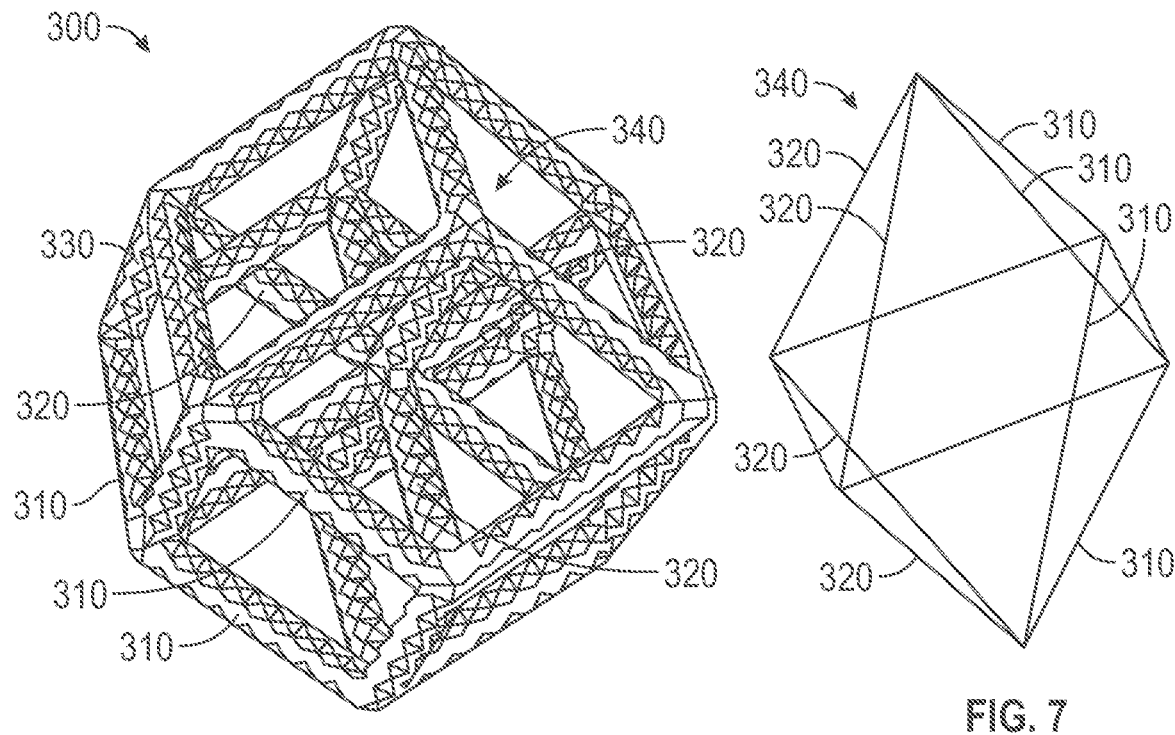
FIG. 6
FIG. 7

(the Y-axis of length represents either pore size or minimum window opening)

THREE-DIMENSIONAL POROUS STRUCTURES FOR BONE INGROWTH AND METHODS FOR PRODUCING

This application claims priority to U.S. Provisional App. No. 62/648,353, which was filed on Mar. 26, 2018 and is expressly incorporated herein by reference.

TECHNICAL FIELD

The embodiments disclosed herein are generally directed towards porous metal structures and methods for manufacturing them, and, more specifically, to porous metal structures in medical devices that have geometric lattice configurations suited to allow for exact control of porosity and pore size in a porous metal structure.

BACKGROUND

The embodiments disclosed herein are generally directed towards three-dimensional porous structures for bone ingrowth and methods for producing said structures.

The field of rapid prototyping and additive manufacturing has seen many advances over the years, particularly for rapid prototyping of articles such as prototype parts and mold dies. These advances have reduced fabrication cost and time, while increasing accuracy of the finished product, versus conventional machining processes, such as those where materials (e.g., metal) start as a block of material, and are consequently machined down to the finished product.

However, the main focus of rapid prototyping three-dimensional structures has been on increasing density of rapid prototyped structures. Examples of modern rapid prototyping/additive manufacturing techniques include sheet lamination, adhesion bonding, laser sintering (or selective laser sintering), laser melting (or selective laser sintering), photopolymerization, droplet deposition, stereolithography, 3D printing, fused deposition modeling, and 3D plotting. Particularly in the areas of selective laser sintering, selective laser melting and 3D printing, the improvement in the production of high density parts has made those techniques useful in designing and accurately producing articles such as highly dense metal parts.

In the past few years, some in the additive manufacturing field have attempted to create solutions that provide the mechanical strength, interconnected channel design, porosity and pore size in porous structures necessary for application in promoting mammalian cell growth and regeneration. However, the current methods and geometries have limited control over the pore size distribution, which exerts a strong influence on the ingrowth behavior of mammalian cells such as bone. Moreover, the current methods and geometries often fall short in producing porous structures having unit cell geometries with pore sizes and porosities simultaneously in the range believed to be beneficial for ingrowth while maintaining structural integrity during the manufacturing process (e.g., 3D printing). As a result, current unit cell geometric structures must either have a very large pore size or very low porosity. Furthermore, current methods and geometries generally prevent close correlation between a selected strut length and diameter of a unit cell, within a structure's geometry, and the resulting geometric features desired in the porous structure.

Current methods of manufacturing porous metal materials for bone ingrowth have limited control over the pore size distribution, which exerts a strong influence on the ingrowth behavior of bone. Better simultaneous control of the maximum pore size, minimum pore size, and porosity would enable better bone ingrowth. Additive manufacturing techniques conceptually enable production of lattice structures with perfect control over the geometry but are practically limited to the minimum lattice strut diameter that the machine can build, and by the need for any lattice structure to be self-supporting. The minimum strut diameter for current 3D printers is approximately 200-250 microns, which means that many geometric structures must either have a very large pore size or very low porosity.

SUMMARY

According to one aspect of the disclosure, geometric structures, and corresponding manufacturing processes, that allow improved simultaneous control of the maximum pore size, minimum pore size, and porosity to enable better bone ingrowth are disclosed. The manufacturing process includes modifying independent strut lengths and/or diameters to achieve desired geometric features (for example, pore size, porosity, window size) in the unit cells of the porous structure. The unit cell geometries disclosed herein enable smaller pore sizes at higher porosities while providing a more homogenous overall structure (i.e., smaller gap between pore size and window size). Structures having unit cells with such robust geometries allow the manufacturing of robust porous structures largely independent of the manufacturing technology used.

According to another aspect, an orthopaedic prosthetic component is disclosed. The orthopaedic prosthetic component comprises a porous three-dimensional structure shaped to be implanted in a patient's body. The porous three-dimensional structure comprises a plurality of connected unit cells, and at least one unit cell comprises a plurality of lattice struts and a plurality of internal struts. The at least one unit cell includes a first geometric structure comprising the plurality of lattice struts, and a plurality of second geometric structures formed out of the plurality of internal struts within the first geometric structure and a number of the lattice struts. Each second geometric structure has an internal volume that is substantially equal to the internal volumes of the other second geometric structures.

In some embodiments, the porous three-dimensional structure may have a porosity between about 50% and about 75%.

In some embodiments, the orthopaedic prosthetic component may comprise a solid base. The porous three-dimensional structure may be attached to the solid base. Additionally, in some embodiments, the base may include a platform and a stem extending away from the platform. The stem extends through the porous three-dimension structure.

In some embodiments, the number of the lattice struts and the plurality of internal struts may define a plurality of openings in the porous three-dimensional structure. Each opening of the plurality of openings may have a window size. The internal volume of each geometric structure may have a pore size, and the ratio of the pore size of each geometric structure to the window size of each opening of the geometric structure may be in a range of 1.00 to 2.90.

In some embodiments, the ratio of the pore size of each geometric structure to the window size of each opening of the geometric structure may be in a range of 1.50 to 1.60. Additionally, in some embodiments, the ratio of the pore size of each geometric structure to the window size of each opening of the geometric structure may be in a range of 1.00 to 1.10.

In some embodiments, the first geometric structure may be a rhombic dodecahedron. Additionally, in some embodiments, each of the plurality of second geometric structures may be a trigonal trapezohedron. In some embodiments, the plurality of second geometric structures may consist of four trigonal trapezohedrons.

In some embodiments, each of the plurality of second geometric structures may be an octahedron.

According to another aspect, an orthopaedic prosthetic component comprises a porous three-dimensional structure shaped to be implanted in a patient's body, and the porous three-dimensional structure comprises a plurality of unit cells. Each unit cell comprises a first geometric structure having a first geometry and comprising a plurality of first struts, and a second geometric structure having a second geometry and comprising a plurality of second struts connected to a number of the plurality of first struts to form the second geometric structure.

In some embodiments, each second geometric structure may have a pore size, and the number of the lattice struts and the plurality of internal struts define a plurality of openings in the porous three-dimensional structure. Each opening of the plurality of openings may have a window size. The ratio of the pore size of each second geometric structure to the window size of each opening of the second geometric structure may be in a range of 1.00 to 2.90.

In some embodiments, the ratio of the pore size of each second geometric structure to the window size of each opening of the second geometric structure may be in a range of 1.50 to 1.60. In some embodiments, the ratio of the pore size of each second geometric structure to the window size of each opening of the second geometric structure may be in a range of 1.00 to 1.10.

In some embodiments, the porous three-dimensional structure may have a porosity that is between about 20% and about 95%.

In some embodiments, the porous three-dimensional structure may have a porosity that is between about 50% and about 75%.

According to another aspect, a method for producing a porous three-dimensional structure is disclosed. The method comprises depositing and scanning successive layers of metal powders with a beam to form a porous three-dimensional structure comprising a plurality of unit cells and having predetermined geometric properties. Each unit cell comprises a plurality of lattice struts and a plurality of internal struts. Each unit cell includes a first geometric structure comprising the plurality of lattice struts, and a plurality of second geometric structures, formed out of the plurality of internal struts within the first geometric structure and a number of lattice struts of the plurality of lattice struts.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIG. 5 is a simplified perspective view of another geometric structure of the unit cell of FIG. 3;

FIG. 6 is a perspective view of another embodiment of a unit cell of a porous structure for the orthopaedic prosthetic component of FIGS. 1-2;

FIG. 7 is a simplified perspective view of another geometric structure of the unit cell of FIG. 3;

DETAILED DESCRIPTION

Figure 1:
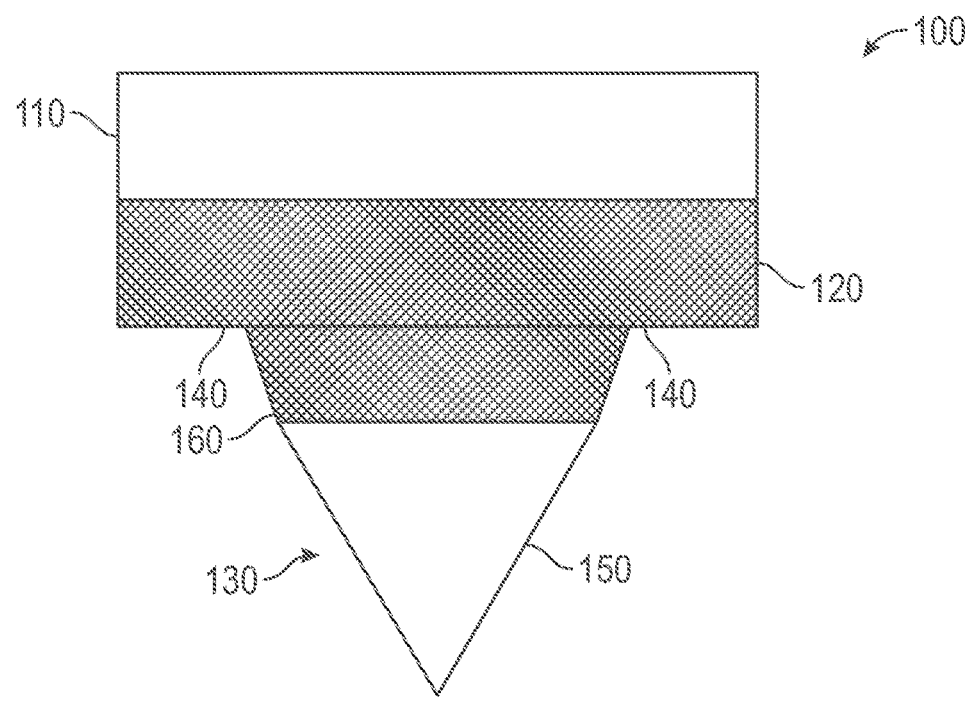
FIG. 1 is a simplified elevation view of an orthopaedic prosthetic component.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a base, etc.) can be "on," "attached to," "connected to," or "coupled to" another element regardless of whether the one element is directly on, attached to, connected to, or coupled to the other element, there are one or more intervening elements between the one element and the other element, or the two elements are integrated as a single piece. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "bonded to" or "bonding" denotes an attachment of metal to metal due to a variety of physicochemical mechanisms, including but not limited to: metallic bonding, electrostatic attraction and/or adhesion forces.

Unless otherwise defined, scientific and technical terms used in connection with the present teachings described herein shall have the meanings that are commonly understood by those of ordinary skill in the art.

The present disclosure relates to porous three-dimensional metallic structures and methods for manufacturing them for medical applications. As described in greater detail below, the porous metallic structures promote hard or soft tissue interlocks between prosthetic components implanted in a patient's body and the patient's surrounding hard or soft tissue. For example, when included on an orthopaedic prosthetic component configured to be implanted in a patient's body, the porous three-dimensional metallic structure can be used to provide a porous outer layer of the orthopaedic prosthetic component to form a bone in-growth structure. Alternatively, the porous three-dimensional metallic structure can be used as an implant with the required structural integrity to both fulfill the intended function of the implant and to provide interconnected porosity for tissue interlock (e.g., bone in-growth) with the surrounding tissue. In various embodiments, the types of metals that can be used to form the porous three-dimensional metallic structures can include, but are not limited to, titanium, titanium alloys, stainless steel, cobalt chrome alloys, tantalum or niobium.

Figure 2:
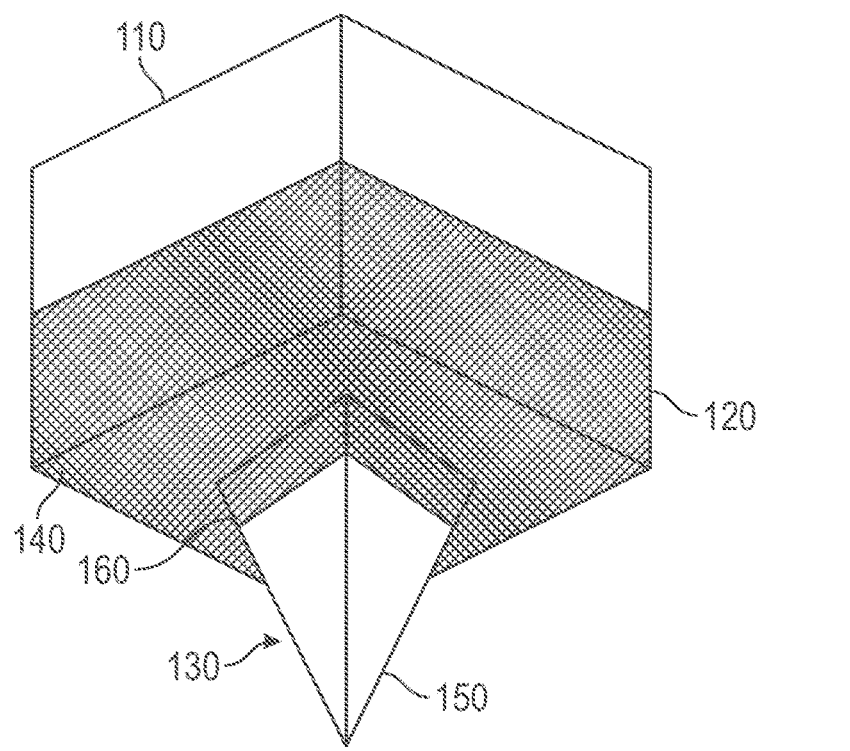
FIG. 2 is a simplified perspective view of the orthopaedic prosthetic component of FIG. 1.

Referring now to FIGS. 1 and 2, an orthopaedic implant or prosthetic component 100 is illustrated. The prosthetic component 100 includes a base 110, a porous three-dimensional structure or layer 120, and a cone or stem 130 extending away from the base 110. In the illustrative embodiment, the porous structure 120 surrounds a portion of the base 110 and a portion of the stem 130. It should be appreciated that the porous structure 120 can be provided as a layer separate from the base 110 and/or the stem 130. The porous structure 120 may also be provided as a coating that surrounds all of the base 110 and/or all of the stem 130. As described in greater detail below, the porous structure includes a plurality of unit cells that define voids or spaces that permit the ingrowth of bone, thereby promoting fixation of the prosthetic component 100 to a patient's bone.

The orthopaedic implant 100 may be implanted into a tibial bone. For example, the stem 130 can be inserted into the tibial bone, with a ledge portion 140 of implant 100 resting against a proximal portion of the tibial bone. It should be appreciated that the various porous structures described herein may be incorporated into various orthopaedic implant designs, including, for example, a tibial prosthetic component or a femoral prosthetic component similar to the tibial and femoral components shown in U.S. Pat. No. 8,470,047, which is expressly incorporated herein by reference. The porous structures may also be included in other orthopaedic implant designs, including a patella component shaped to engage a femoral prosthetic component and prosthetic components for use in a hip or shoulder arthroplasty surgery It should also be noted, for the preceding and going forward, that the base 110 can be any type of structure capable of, for example, contacting, supporting, connecting to or with, or anchoring to or with components of various embodiments herein. The base 110 can include, for example, a metal or non-metal tray, a metal or non-metal baseplate, a metal or non-metal structure that sits on a tray, and so on. The types of metal that can be used to form the base 110 include, but are not limited to, titanium, titanium alloys, stainless steel, cobalt chrome alloys, tantalum or niobium.

In the illustrative embodiment, the stem 130 includes a solid region 150, which is coated by a porous region 160 of the porous structure 120. The solid region 150 of the stem 130 is anchored to the base 110 and extends outwardly from the porous structure 120 such that the porous structure 120 surrounds the region of stem 130 proximal to base 110. In other embodiments, the stem 130 may be anchored to the porous structure 120. The types of metal that can be used to form the stem 130 include, but are not limited to, titanium, titanium alloys, stainless steel, cobalt chrome alloys, tantalum or niobium.

Figure 3:
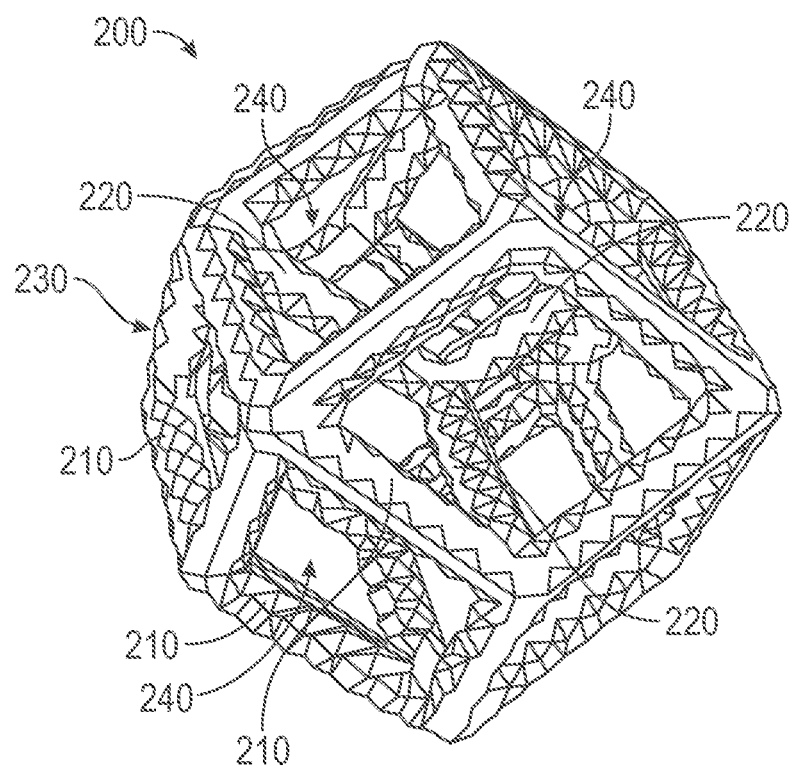
FIG. 3 is a perspective view of a unit cell of the porous structure of the orthopaedic prosthetic component of FIGS. 1-2.
Figure 4:
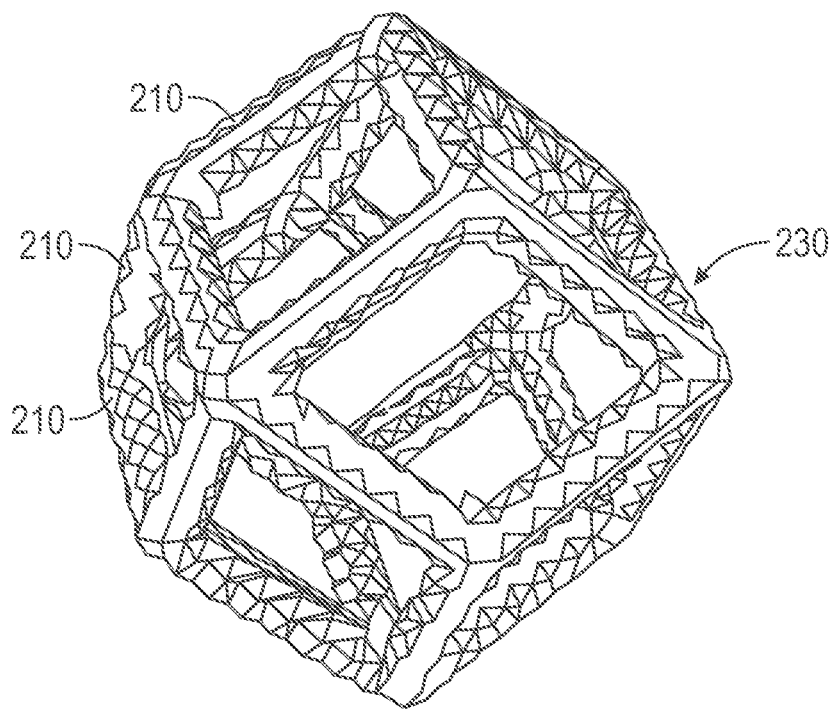
FIG. 4 is a perspective view of one geometric structure of the unit cell of FIG. 3.

Referring now to FIG. 3, the porous structure 120 of the implant 100 includes a plurality of connected unit cells, and each unit cell illustratively has the unit cell structure 200 shown in FIG. 3. The types of metal that can be used to form the unit cell structures shown in include, but are not limited to, titanium, titanium alloys, stainless steel, cobalt chrome alloys, tantalum or niobium. As shown in FIG. 3, each structure 200 includes a plurality of lattice struts 210 and a plurality of internal struts 220, which form a first geometric structure 230 and a plurality of second geometric structures 240 that are within the first geometric structure 230. In the illustrative embodiment, the first geometric structure 230 comprises the plurality of lattice struts 210. As shown in FIG. 4, the plurality of lattice struts 210 cooperate to form a rhombic dodecahedron.

Each of the plurality of second geometric structures 240 has an internal volume 250 that is substantially equal to the internal volumes 250 of the other second geometric structures 240. As shown in FIG. 5, each second geometric structure 240 is formed by a number of internal struts 220 and a number of lattice struts 210. Each second geometric structure 240 is illustratively a trigonal trapezohedron. As illustrated in FIG. 3, the plurality of second geometric structures 240 within the first geometric structure 230 include four trigonal trapezohedrons such that the unit cell structure 200 is a rhombic trigonal trapezohedron.

It should be appreciated that each unit cell structure may include other types of second geometric structures. For example, as shown in FIG. 6, a unit cell structure 300 includes a plurality of lattice struts 310 and a plurality of internal struts 320, which form a first geometric structure 330 and a plurality of second geometric structures 340 that are within the first geometric structure 330. In the illustrative embodiment, the first geometric structure 330, like the first geometric structure 230, comprises the plurality of lattice struts 310 and is a rhombic dodecahedron.

As shown in FIG. 7, each second geometric structure 340 is formed by a number of internal struts 320 and a number of lattice struts 310. Each second geometric structure 340 is illustratively an octahedron (e.g., a diamond-shaped structure). As illustrated in FIG. 6, the plurality of second geometric structures 340 within the first geometric structure 330 include six octahedrons such that the unit cell structure 300 is a rhombic octahedron.

Within the unit cell structures of the porous three-dimensional structure described above, at least one of a length and diameter of at least one strut within each unit cell can be modified to meet predetermined or desired geometric properties of the lattice. These geometric properties can be selected from the group consisting of porosity, pore size, minimum window size, and combinations thereof. It was advantageously discovered that certain geometric structures (discussed below) of the unit cell structure could optimize one or more of these geometric properties to provide a more robust, and homogenous, geometry. The resulting geometry provides for more optimal bone ingrowth while maintaining the requisite porous structure stability.

Figure 8:
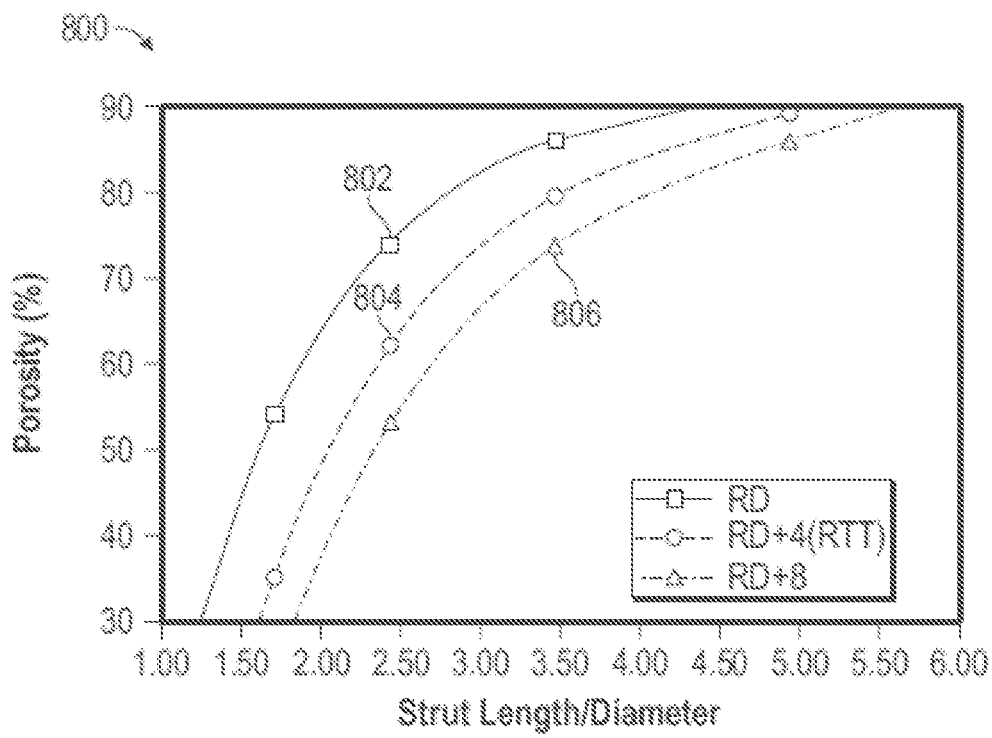
FIG. 8 illustrates a chart of porosity percentage versus strut length/diameter for various unit cell geometries, in accordance with various embodiments.

Turning to porosity, the porous structure 120 has a porosity of between about 50% and about 75%. As used herein, the term "about" refers to a range associated with typical manufacturing tolerances. In that way, a porosity of "about 50%" may be porosity of 50% plus or minus a typical manufacturing tolerance such as, for example, 2% (i.e., a range of 48% to 52%). In other embodiments, the porosity of the porous three-dimensional structure is between about 20% and about 95%. In other embodiments, the porosity is in a range of between about 35% and about 85%. Geometrically, the porosity of the unit cell structure is dependent on the ratio of the strut length (a) to the strut diameter (d). FIG. 8, for example, a chart 800 of porosity percentage versus strut length/diameter for various unit cell geometries is provided, in accordance with various embodiments. As outlined in the chart 800, three particular unit cell geometries/structures were examined, namely a rhombic dodecahedron (RD) (see, e.g., FIG. 4), a rhombic dodecahedron provided with four internal struts (RD+4) (or rhombic trigonal trapezohedron) (see, e.g., FIG. 3), and a rhombic dodecahedron provided with eight internal struts (RD+8) (or rhombic octahedron) (see, e.g., FIG. 6). For each of the structures, porosities were obtained at several a/d ratios from a design file for each unit cell structure and the relationship for each unit cell structure modeled by fitting the data to a fourth order polynomial equation of the form:

$$\text{Porosity} = A*(a/d)^4 + B*(a/d)^3 + C*(a/d)^2 + D*(a/d) + E \tag{1}$$

Wherein A, B, C, D, and E are constants. In this comparison, the structure dimensions were derived geometrically from the strut length and diameter of each unit cell structure.

As observed in the chart 800 of FIG. 8, the RD structure generally possesses a greater porosity at a given a/d ratio, which is to be expected given its lack of internal struts compared to the RD+4 and RD+8 structures. The porosity for the RD structure is illustrated by the line 802. However, this decrease in porosity in the RD+4 and RD+8 structures, illustrated by lines 804, 806, respectively, enables designs made with them to reach combinations of relatively lower porosity, lower pore size, and relatively higher window size at a constant strut diameter (fixed by the build resolution of the printer) not possible with the RD, as described in greater detail below.

Figure 9:
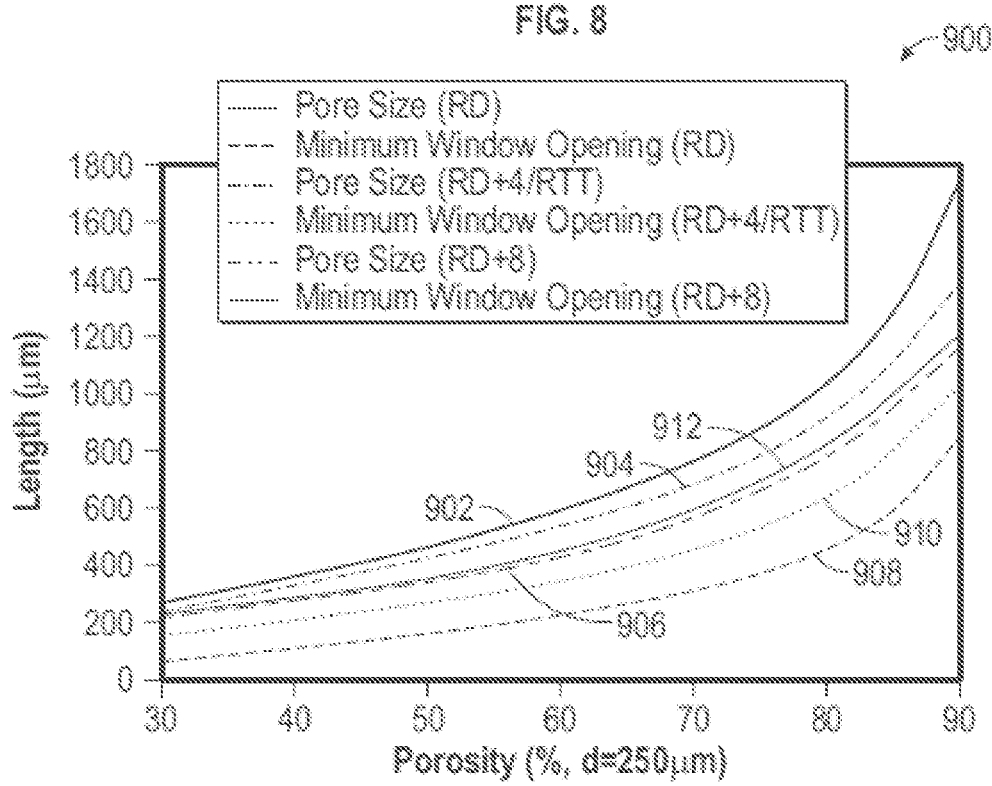
FIG. 9 illustrates a chart of pore size and minimum pore window opening size versus porosity percentage for various unit cell geometries, in accordance with various embodiments.

Referring now to FIG. 9, a chart 900 of pore size and minimum window size versus porosity percentage for various unit cell geometries/structures is provided, in accordance with various embodiments. As in FIG. 8, three particular unit cell structures were examined, namely a rhombic dodecahedron (RD) (see, e.g., FIG. 4), a rhombic dodecahedron provided with four internal struts (RD+4) (or rhombic trigonal trapezohedron) (see, e.g., FIG. 3), and a rhombic dodecahedron provided with eight internal struts (RD+8) (or rhombic octahedron) (see, e.g., FIG. 6). The pore size of the rhombic dodecahedron, for example, was taken as the equivalent diameter of a sphere within the volume bounded within the rhombic dodecahedron unit cell, and the volume was calculated by taking the volume of the rhombic dodecahedron of strut length (a) and subtracting the volume of each strut within or bounded by the rhombic dodecahedron. The equations provided herein for calculating pore size (PS) depend on the strut length (a), diameter (d), and porosity in decimal units (p). The equations are as follows:

For the RD structure:

$$PS = a*\sqrt[3]{6/\pi}*\sqrt[3]{\frac{16*\sqrt{3}*p}{9} - \frac{4d}{a}*\left(1 - \frac{\sqrt{2}\,d}{2a}\right)^2} \tag{2}$$

For the RD+4 structure:

$$PS = \sqrt[3]{\frac{6}{4\pi}*\left[\begin{array}{l}(1-\{1-p\})*\left(\frac{16}{9}*\sqrt[2]{3}*a^3\right)-0.5* \\ (\pi*d^2*\{\sqrt[2]{3}*a-0.75*d\}-d^3*\{4-2\sqrt[2]{2}\})\end{array}\right]} \tag{3}$$

For the RD+8 structure:

$$PS = \sqrt[3]{\frac{6}{8\pi}*\left[\begin{array}{l}(1-\{1-p\})*\left(\frac{16}{9}*\sqrt[2]{3}*a^3\right)-\pi*d^2* \\ \{2a-d\}+4.5d^3*\{2\sqrt[2]{2}-2\sqrt[2]{6}\}\end{array}\right]} \tag{4}$$

The line 902 in the chart 900 illustrates the relationship between pore size and porosity percentage for the rhombic dodecahedron (RD). The line 904 illustrates the relationship between pore size and porosity percentage for the rhombic trigonal trapezohedron (RD+4), and the line 906 illustrates the relationship between pore size and porosity percentage for the rhombic octahedron (RD+8).

As observed in the chart 900 of FIG. 9, at lower porosity percentages, the three structures generally provided similar required pore sizes. However, as the given porosity percentage increases (and assuming that the strut diameters remain substantially the same), the required pore size in the RD structure to accommodate the porosity percentage becomes significantly greater than the other structures, thus putting more stringent requirements on the RD structure as required porosity increases by causing the pore size to increase to beyond what may be effective for bone in-growth. In other words, as required porosity percentage increases, the less effective the RD structure becomes, which is noteworthy when designing porous three-dimensional structures such as those discussed herein.

Figure 10:
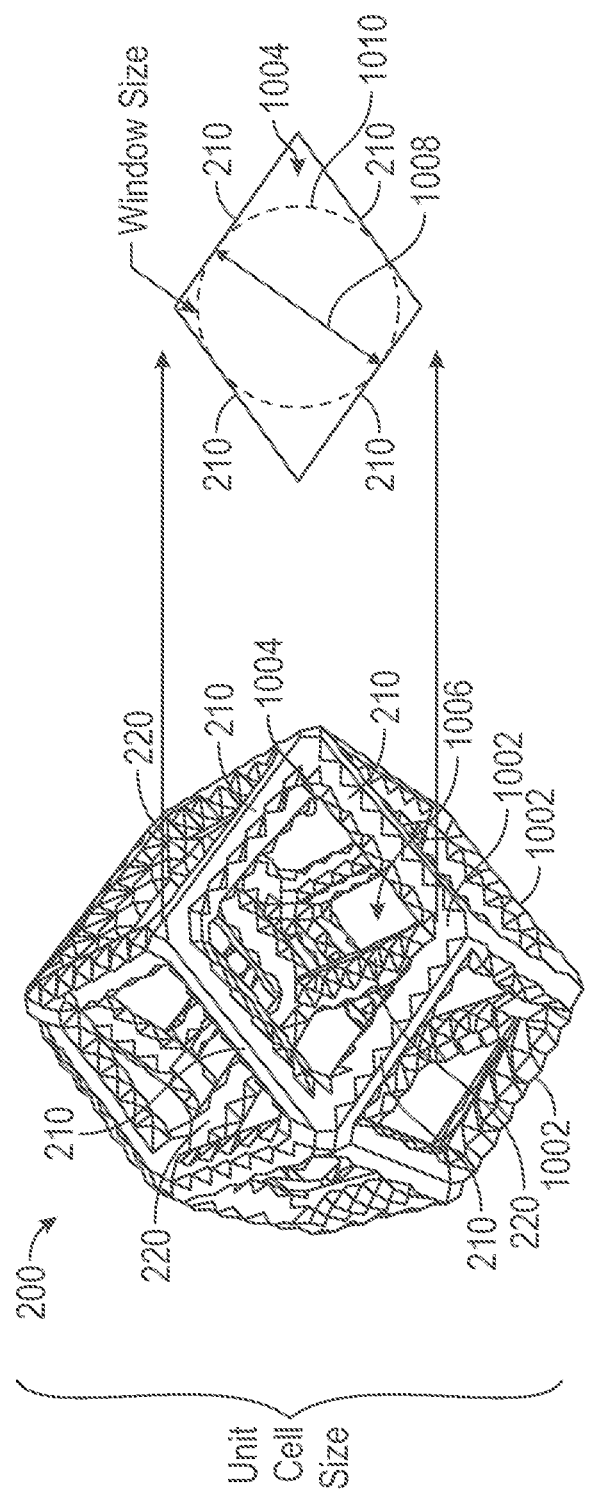
FIG. 10 illustrates an association of window size to a unit cell structure, in accordance with various embodiments.

Referring now to FIG. 10, each unit cell structure 200 has a plurality of outer faces 1002 and the lattice struts 210 cooperate to define a number of openings 1004 in the outer faces 1002. The internal struts 220 of the unit cell structure 200 cooperate with a number of lattice struts 210 to form a number of internal openings 1006. The minimum window opening or size of each of the openings 1004, 1006 may be defined as the diameter 1008 of a circle 1010 positioned in the corresponding opening (illustratively one of the openings 1004 in FIG. 10) such that each strut 210 (or strut 220) is positioned on a tangent line of the circle 1010. The lengths and diameters of the struts thereby determine the size of each of the openings 1004, 1006 and, by extension, the diameter of the largest sphere that can fit therein. For example, for a given strut length, as the strut diameter increases, the minimum window opening would decrease.

These associations are provided by the following equation, which was used to calculate minimum window opening for all structures (e.g., RD, RD+4, RD+8, etc.) and generate the lines 908, 910, 912 in FIG. 9:

$$m = 2/3\sqrt{2^*}a - d \tag{5}$$

For the purposes of the chart 900, the minimum window opening is the diameter of the largest circle 1010 that can fit in each opening. In other words, it is the diameter of the inscribed circle and, as such, is dependent on the strut length (a) and diameter (d). The relationship between window size versus porosity percentage for various unit cell geometries. The line 908 in the chart 900 illustrates the relationship between minimum window opening versus porosity for the rhombic dodecahedron (RD). The line 910 illustrates the relationship between minimum window opening versus porosity for the rhombic trigonal trapezohedron (RD+4), and the line 912 illustrates the relationship between minimum window opening versus porosity for the rhombic octahedron (RD+8).

As observed on the chart 900 in FIG. 9, at generally all porosity percentages, there exists a generally uniform gap in the minimum window opening for between each unit cell structure. As such, regardless of required porosity percentage for a given porous three-dimensional structure with a substantially constant strut diameter, the RD+8 structure will possess a greater minimum window opening than the RD+4 and RD structures, and both the RD+8 and RD+4 structures will possess a greater minimum window opening than the RD structure, to a given porosity percentage.

The results in FIG. 9 establish that the structures having internal struts, namely RD+4, and to a lesser extent RD+8, are advantageous over the RD structure. The RD+4 and RD+8 enable smaller pore size at a given porosity and strut diameter. Whatever advantage the RD structure would seem to have in porosity as a function of a/d ratio almost entirely diminishes as the required a/d ratio increases. Finally, the RD+4 and RD+8 structures (or structures with internal struts) provide the most homogenous structure by providing a smaller difference between pore size and window size than the RD structure.

In the porous structure 120, the ratio of the pore size of a unit cell to any of its corresponding window sizes is in a range of 1.50 to 1.60. In other embodiments, the ratio may be in a range of 1.00 to 1.10. In still other embodiments, the ratio may be 1.00 to 2.90. As shown in FIG. 9, the difference between pore size and window size is substantially less for the RTT structure of FIGS. 3 and 6 than the RD structure. As a consequence, the RTT structure advantageously provides for a more homogeneous structure, with a smaller difference between the pore window size and overall pore size, especially at high levels of porosity, which promotes bone in-growth by providing window sizes closely in proportion of the pore size. Though only RTT is referenced in this figure, the conclusion would hold for various structures that include internal struts, for example, structures with internal struts in multiples of four.

In accordance with various embodiments, an orthopaedic implant is provided. The implant can include a porous three-dimensional structure comprising a lattice of connected unit cells, as illustrated, for example, by the unit cell structure of FIGS. 3-5. The at least one unit cell can comprise a plurality of lattice struts. The at least one unit cell can further comprise a first geometric structure comprising the plurality of lattice struts, and a second geometric structure sharing a subset of the plurality of lattice struts of the first geometric structure and having a different geometry from the first geometric structure (see FIGS. 3 and 6). Further, at least a portion of the subset of the plurality of lattice struts in the second geometric structure can intersect to form angles substantially equal to the angles formed by intersections of the plurality of lattice struts of the first geometric structure.

As discussed above, the first geometric structure can be a rhombic dodecahedron as illustrated, for example, in FIG. 4. The second geometric structure can be a trigonal trapezohedron (see FIG. 5). The trigonal trapezohedron can be formed by inserting four struts into the first geometric structure as illustrated, for example, in FIG. 3. Further, the at least one unit cell can include four trigonal trapezohedron geometric structures within the first geometric structure as illustrated, for example, in FIG. 3.

Within the porous three-dimensional structure, at least one of a length and diameter of at least one strut within the lattice can be modified to meet predetermined geometric properties of the lattice. As discussed above, these geometric properties can be selected from the group consisting of, porosity, pore size, minimum opening size, and combinations thereof. For example, the porosity can be between about 20% and about 95%. The porosity can also be between about 35% and about 85%. The porosity can also be between about 50% and about 75%. Further, the individual strut lengths can be modified to be, for example, about 25% to about 175% of the average strut length of the plurality of struts. The individual lattice strut lengths can also be modified to be, for example, about 50% to about 150% of the average strut length of the plurality of lattice struts. The individual lattice strut lengths can also be modified to be, for example, about 75% to about 125% of the average strut length of the plurality of lattice struts.

In accordance with various embodiments, an orthopaedic implant is provided. The implant can include a porous three-dimensional structure comprising a plurality of repeating unit cells, with each unit cell comprising a plurality of struts. Each unit cell can include a base geometric structure, and a secondary geometric structure formed out of a portion of the base geometric structure and having a different geometry from the base geometric structure. Further, for a given porous three-dimensional structure porosity, at least one unit cell can have a pore size that is different from the average geometric structure pore size of the porous three-dimensional structure and a window size that is different from the average geometric structure window size of the porous three-dimensional structure.

Within the porous three-dimensional structure, at least one of a length and diameter of at least one strut within the unit cell can be modified to meet predetermined geometric properties of the unit cell. As discussed above, the geometric properties can be selected from the group consisting of, porosity, pore size, minimum opening size, and combinations thereof. For example, the porosity can be between about 20% and about 95%. The porosity can also be between about 35% and about 85%. The porosity can also be between about 50% and about 75%. Moreover, strut lengths can be modified to be about 25% to about 175% of the average strut length of the plurality of struts. The individual lattice strut lengths can also be modified to be, for example, about 50% to about 150% of the average strut length of the plurality of lattice struts. The individual lattice strut lengths can also be modified to be, for example, about 75% to about 125% of the average strut length of the plurality of lattice struts.

As discussed above, the first geometric structure can be a rhombic dodecahedron. The second geometric structure can be a trigonal trapezohedron. The trigonal trapezohedron can be formed by inserting four struts into the first geometric structure. Further, the at least one unit cell can include four trigonal trapezohedron geometric structures within the first geometric structure.

In accordance with various embodiments, an orthopaedic implant is provided. The implant can include a porous three-dimensional structure comprising a plurality of unit cells. Each unit cell can comprise an outer geometric structure having a first geometry and comprising a plurality of first struts. Each unit cell can further comprise an inner geometric structure having a second geometry and further comprise a plurality of second struts connected to a portion of the plurality of first struts to form the inner geometric structure within the outer geometric structure.

In accordance with various embodiments, the outer geometric structure can be a rhombic dodecahedron. The inner geometric structure can be a trigonal trapezohedron. The trigonal trapezohedron can be formed by inserting four struts into the outer geometric structure. Further, the at least one unit cell can include four trigonal trapezohedron geometric structures within the outer geometric structure.

Manufacturing Processes

The porous three-dimensional metallic structures disclosed above can be made using a variety of different metal component manufacturing techniques, including but not limited to: Casting Processes (casting processes involve pouring molten metal into a mold cavity where, once solid, the metal can take on the shape of the cavity. Examples include, expendable mold casting, permanent mold casting, and powder compaction metallurgy), Deformation Processes (deformation processes include metal forming and sheet metalworking processes which involve the use of a tool that applies mechanical stresses to metal which exceed the yield stress of the metal), Material Removal Processes (these processes remove extra material from the workpiece in order to achieve the desired shape. Examples of material removal processes include, tool machining and abrasive machining), and Additive Manufacturing Processes (these processes involve the use of digital 3D design data to build up a metal component up in layers by depositing successive layers of material). Additive Manufacturing Processes can include, only by way of example, powder bed fusion printing method (e.g., melting and sintering), cold spray 3D printing, wire feed 3D printing, fused deposition 3D printing, extrusion 3D printing, liquid metal 3D printing, stereolithography 3D printing, binder jetting 3D printing, material jetting 3D printing, and so on. It should be appreciated, however, that additive manufacturing processes offer some unique advantages over the other metal component manufacturing techniques with respect to the manufacture of porous three-dimensional metallic structures (disclosed above) due to the complexities of the geometries and structural elements of the unit cells which comprise those types of structures.

Figure 11:
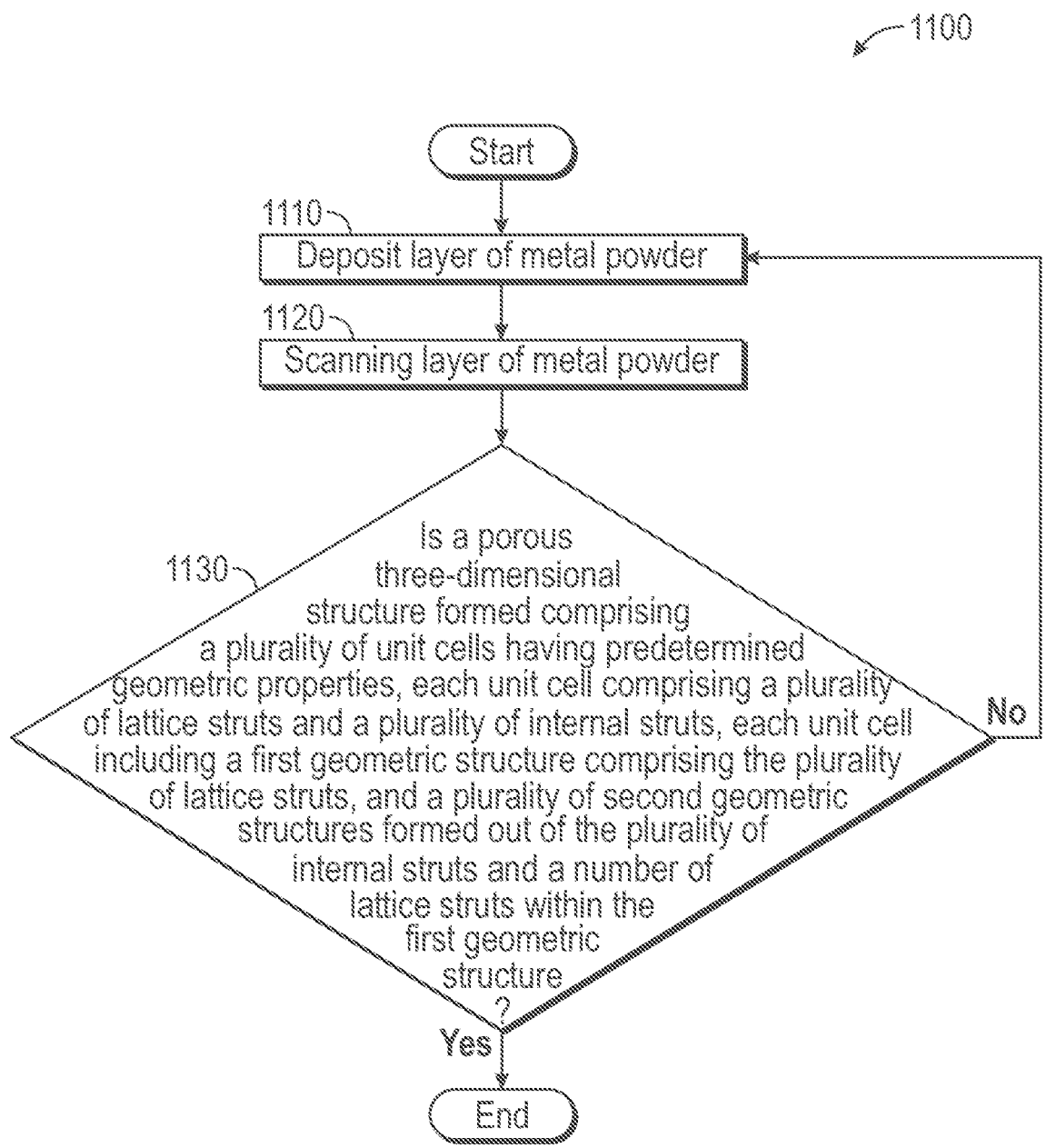
FIG. 11 illustrates a workflow for producing a porous three-dimensional structure, in accordance with various embodiments.

In accordance with various embodiments, a method for producing a porous three-dimensional structure is provided, for example, by method 1100 illustrated in FIG. 11. The method can comprise depositing and scanning successive layers of metal powders with a beam to form a porous three-dimensional structure. The porous three-dimensional structure can comprise a plurality of unit cells having predetermined geometric properties, and each unit cell can comprise a plurality of lattice struts and a plurality of internal struts. Each unit cell further includes a first geometric structure comprising the plurality of lattice struts and a plurality of second geometric structures, formed out of the plurality of internal struts within the first geometric structure. The beam (or scanning beam) can be an electron beam. The beam (or scanning beam) can be a laser beam.

As provided in FIG. 11, the method 1100 may begin with a step 1110, which includes depositing a layer of metal powder. The method may continue with a step 1120, which includes scanning a layer of metal powder. As provided in a step 1130, the steps 1110 and 1120 are repeated until a porous three-dimensional structure is formed comprising a plurality of unit cells having predetermined geometric properties. Each unit cell comprises a plurality of lattice struts and a plurality of internal struts. Each unit cell including a first geometric structure comprising the plurality of lattice struts, and a plurality of second geometric structures formed out of a number of internal struts within the first geometric structure and a number of lattice struts.

Regarding the various methods described herein, the metal powders can be sintered to form the porous three-dimensional structure. Alternatively, the metal powders can be melted to form the porous three-dimensional structure. The successive layers of metal powders can be deposited onto a solid base (see above for discussion regarding base). In various embodiments, the types of metal powders that can be used include, but are not limited to, titanium, titanium alloys, stainless steel, cobalt chrome alloys, tantalum or niobium powders.

Regarding the various methods described herein, the geometric properties can be selected from the group consisting of, porosity, pore size, minimum opening size, and combinations thereof. The porosity can be between about 20% and about 95%. The porosity can also be between about 40% and about 80%. The porosity can also be between about 50% and about 75%. Moreover, strut lengths can be modified to be about 25% to about 175% of the average strut length of the plurality of struts. The individual lattice strut lengths can also be modified to be, for example, about 50% to about 150% of the average strut length of the plurality of lattice struts. The individual lattice strut lengths can also be modified to be, for example, about 75% to about 125% of the average strut length of the plurality of lattice struts. Further, the unit cell can have a pore size less than the first geometric structure pore size. Moreover, the unit cell can have a window size greater than the window size of each of the plurality of second geometric structures.

Regarding the various methods described, the first geometric structure can be a rhombic dodecahedron. Each of the second geometric structures can be a trigonal trapezohedron. The trigonal trapezohedron can be formed by inserting four struts into the first geometric structure. Further, the at least one unit cell can include four trigonal trapezohedron geometric structures within the first geometric structure.

In various embodiments, a method for producing a porous three-dimensional structure is provided, the method comprising applying a stream of metal particles at a predetermined velocity onto a base to form a porous three-dimensional structure comprising a plurality of unit cells and having predetermined geometric properties, each unit cell comprising a plurality of lattice struts and a plurality of internal struts. Each unit cell can include, a first geometric structure comprising the plurality of lattice struts, and a plurality of second geometric structures, formed out of the plurality of internal struts within the first geometric structure. In various embodiments, the types of metal particles that can be used include, but are not limited to, titanium, titanium alloys, stainless steel, cobalt chrome alloys, tantalum or niobium particles.

The predetermined velocity can be a critical velocity required for the metal particles to bond upon impacting the base. The critical velocity is greater than 340 m/s.

The method can further include applying a laser at a predetermined power setting onto an area of the base where the stream of metal particles is impacting The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can be formed, for example, by inserting eight internal struts into a first geometric structure. In this case, six octahedron geometric structures can be provided within the first geometric structure.

In accordance with various embodiments, a method for producing a porous three-dimensional structure is provided, the method comprising introducing a continuous feed of metal wire onto a base surface and applying a beam at a predetermined power setting to an area where the metal wire contacts the base surface to form a porous three-dimensional structure comprising a plurality of unit cells and having predetermined geometric properties. Each unit cell can comprise a plurality of lattice struts and a plurality of internal struts, each unit cell including a first geometric structure comprising the plurality of lattice struts, and a plurality of second geometric structures, formed out of the plurality of internal struts within the first geometric structure. The beam (or scanning beam) can be an electron beam. The beam (or scanning beam) can be a laser beam. In various embodiments, the types of metal wire that can be used include, but are not limited to, titanium, titanium alloys, stainless steel, cobalt chrome alloys, tantalum or niobium wire.

The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can be formed, for example, by inserting eight internal struts into a first geometric structure. That is, six octahedron geometric structures can be provided within the first geometric structure.

In accordance with various embodiments, a method for producing a porous three-dimensional structure is provided, the method comprising introducing a continuous feed of a polymer material embedded with metal elements onto a base surface. The method can further comprise applying heat to an area where the polymer material contacts the base surface to form a porous three-dimensional structure comprising a plurality of unit cells and having predetermined geometric properties. Each unit cell can comprise a plurality of lattice struts and a plurality of internal struts. Each unit cell includes a first geometric structure comprising the plurality of lattice struts, and a plurality of second geometric structures, formed out of a number of the internal struts within the first geometric structure and a number of lattice struts. The metal elements can be a metal powder. In various embodiments, the continuous feed of the polymer material can be supplied through a heated nozzle thus eliminating the need to apply heat to the area where the polymer material contacts the base surface to form the porous three-dimensional structure. In various embodiments, the types of metal elements that can be used to embed the polymer material can include, but are not limited to, titanium, titanium alloys, stainless steel, cobalt chrome alloys, tantalum or niobium.

The method can further comprise scanning the porous three-dimensional structure with a beam to burn off the polymer material. The beam (or scanning beam) can be an electron beam. The beam (or scanning beam) can be a laser beam.

The first geometric structure can be a rhombic dodecahedron. In various embodiments, each of the second geometric structures can be a trigonal trapezohedron. That is, four trigonal trapezohedrons can be formed by inserting four struts into the first geometric structure. In various embodiments, octahedrons can be formed, for example, by inserting eight internal struts into a first geometric structure. That is, six octahedron geometric structures can be provided within the first geometric structure.

In accordance with various embodiments, a method for producing a porous three-dimensional structure is provided, the method comprising introducing a metal slurry through a nozzle onto a base surface to form a porous three-dimensional structure comprising a plurality of unit cells and having predetermined geometric properties. Each unit cell can comprise a plurality of lattice struts and a plurality of internal struts. Each unit cell can include a first geometric structure comprising the plurality of lattice struts, and a plurality of second geometric structures, formed out of a number of the internal struts within the first geometric structure and a number of the lattice struts. In various embodiments, the nozzle is heated at a temperature required to bond metallic elements of the metal slurry to the base surface. In various embodiments, the metal slurry is an aqueous suspension containing metal particles along with one or more additives (liquid or solid) to improve the performance of the manufacturing process or the porous three-dimensional structure. In various embodiments, the metal slurry is an organic solvent suspension containing metal particles along with one or more additives (liquid or solid) to improve the performance of the manufacturing process or the porous three-dimensional structure. In various embodiments, the types of metal particles that can be utilized in the metal slurry include, but are not limited to, titanium, titanium alloys, stainless steel, cobalt chrome alloys, tantalum or niobium particles.

The first geometric structure can be a rhombic dodecahedron. In some embodiments, each of the second geometric structures can be a trigonal trapezohedron. That is, four trigonal trapezohedrons can be formed by inserting four struts into the first geometric structure. In various embodiments, octahedrons can be formed, for example, by inserting eight internal struts into a first geometric structure. That is six octahedron geometric structures can be provided within the first geometric structure.

In accordance with various embodiments, a method for producing a porous three-dimensional structure is provided, the method comprising introducing successive layers of molten metal onto a base surface to form a porous three-dimensional structure comprising a plurality of unit cells and having predetermined geometric properties. Each unit cell can comprise a plurality of lattice struts and a plurality of internal struts. Each unit cell can include a first geometric structure comprising the plurality of lattice struts, and a plurality of second geometric structures, formed out of the plurality of internal struts within the first geometric structure and a number of the lattice struts. Further, the molten metal can be introduced as a continuous stream onto the base surface. The molten metal can also be introduced as a stream of discrete molten metal droplets onto the base surface. In various embodiments, the types of molten metals that can be used include, but are not limited to, titanium, titanium alloys, stainless steel, cobalt chrome alloys, tantalum or niobium.

The first geometric structure can be a rhombic dodecahedron. In various embodiments, each of the second geometric structures can be a trigonal trapezohedron. That is, four trigonal trapezohedrons can be formed by inserting four struts into the first geometric structure. In various embodiments, octahedrons can be formed, for example, by inserting eight internal struts into a first geometric structure. That is, six octahedron geometric structures can be provided within the first geometric structure.

In accordance with various embodiments, a method for producing a porous three-dimensional structure is provided, the method comprising applying and photoactivating successive layers of photosensitive polymer embedded with metal elements onto a base surface to form a porous three-dimensional structure comprising a plurality of unit cells and having predetermined geometric properties. Each unit cell can comprise a plurality of lattice struts and a plurality of internal struts. Each unit cell can include a first geometric structure comprising the plurality of lattice struts, and a plurality of second geometric structures, formed out of the plurality of internal struts within the first geometric structure and a number of the lattice struts. In various embodiments, the types of metal elements that can be used to embed the polymer material can include, but are not limited to, titanium, titanium alloys, stainless steel, cobalt chrome alloys, tantalum or niobium.

The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can be formed, for example, by inserting eight internal struts into a first geometric structure. That is, six octahedron geometric structures can be provided within the first geometric structure.

In accordance with various embodiments, a method for producing a porous three-dimensional structure is provided, the method comprising depositing and binding successive layers of metal powders with a binder material to form a porous three-dimensional structure comprising a plurality of unit cells and having predetermined geometric properties. Each unit cell can comprise a plurality of lattice struts and a plurality of internal struts. Each unit cell can include a first geometric structure comprising the plurality of lattice struts, and a plurality of second geometric structures, formed out of the plurality of internal struts within the first geometric structure and a number of the lattice struts. In various embodiments, the types of metal powders that can be used include, but are not limited to, titanium, titanium alloys, stainless steel, cobalt chrome alloys, tantalum or niobium powders.

The method can further include sintering the bound metal powder with a beam. The beam (or scanning beam) can be an electron beam. The beam (or scanning beam) can be a laser beam.

The method can further include melting the bound metal powder with a beam. The beam (or scanning beam) can be an electron beam. The beam (or scanning beam) can be a laser beam.

The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can also be formed, for example, by inserting eight internal struts into a first geometric structure. That is, six octahedron geometric structures can be provided within the first geometric structure.

In accordance with various embodiments, a method for producing a porous three-dimensional structure is provided, the method comprising depositing droplets of a metal material onto a base surface, and applying heat to an area where the metal material contacts the base surface to form a porous three-dimensional structure comprising a plurality of unit cells and having predetermined geometric properties. Each unit cell can comprise a plurality of lattice struts and a plurality of internal struts. Each unit cell can include a first geometric structure comprising the plurality of lattice struts, and a plurality of second geometric structures, formed out of the plurality of internal struts within the first geometric structure and a number of the lattice struts. The beam (or scanning beam) can be an electron beam. The beam (or scanning beam) can be a laser beam. In various embodiments, the types of metal materials that can be used include, but are not limited to, titanium, titanium alloys, stainless steel, cobalt chrome alloys, tantalum or niobium.

The deposited droplets of metal material can be a metal slurry embedded with metallic elements. The metal material can be a metal powder.

The first geometric structure can be a rhombic dodecahedron. In some embodiments, each of the second geometric structures can be a trigonal trapezohedron. That is, four trigonal trapezohedrons can be formed by inserting four struts into the first geometric structure. In some embodiments, octahedrons can be formed, for example, by inserting eight internal struts into a first geometric structure. That is, six octahedron geometric structures can be provided within the first geometric structure.

Although specific embodiments and applications of the same have been described in this specification, these embodiments and applications are exemplary only, and many variations are possible.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed:

1. An orthopaedic prosthetic component, comprising:
a porous three-dimensional structure shaped to be implanted in a patient's body, the porous three-dimensional structure comprising a plurality of connected unit cells,
wherein at least one unit cell of the plurality of connected unit cells includes:
a first structure comprising a plurality of lattice struts arranged such that the first structure is a rhombic dodecahedron, and
a plurality of second structures each formed out of a respective plurality of internal struts within the first structure and a respective number of the lattice struts,
wherein:
the respective number of the lattice struts and the respective plurality of internal struts of the second structures define respective pluralities of openings in the porous three-dimensional structure, each opening of the plurality of openings having a window size,
each second structure has a respective internal volume that, in turn, has a respective pore size, and
for each second structure, a ratio of the respective pore size to each window size is in a range of 1.00 to 2.90.

2. The orthopaedic prosthetic component of claim 1, wherein the porous three-dimensional structure has a porosity between about 50% and about 75%.

3. The orthopaedic prosthetic component of claim 1, further comprising a solid base, wherein the porous three-dimensional structure is attached to the solid base.

4. The orthopaedic prosthetic component of claim 3, wherein the solid base includes a platform and a stem extending away from the platform, the stem extending through the porous three-dimensional structure.

5. The orthopaedic prosthetic component of claim 1, wherein the ratio is in a range of 1.50 to 1.60.

6. The orthopaedic prosthetic component of claim 1, wherein the ratio is in a range of 1.00 to 1.10.

7. The orthopaedic prosthetic component of claim 1, wherein each of the plurality of second structures is a trigonal trapezohedron.

8. The orthopaedic prosthetic component of claim 1, wherein the plurality of second structures consists of four trigonal trapezohedrons.

9. The orthopaedic prosthetic component of claim 1, wherein each of the plurality of second structures is an octahedron.

10. An orthopaedic prosthetic component, comprising:
a porous three-dimensional structure shaped to be implanted in a patient's body, the porous three-dimensional structure comprising a plurality of unit cells,
wherein each unit cell of the plurality of unit cells comprises a first structure having a first geometry and comprising a plurality of first struts, and a second structure having a second geometry and comprising a plurality of second struts connected to a number of the plurality of first struts to form the second structure, wherein:
the second structure has a pore size,
the number of the plurality of first struts and the plurality of second struts define a plurality of openings in the porous three-dimensional structure, each opening of the plurality of openings having a window size, and
the pore size and the window size of each opening of the plurality of openings defines a ratio of pore size to window size that is in a range of 1.50 to 1.60.

11. The orthopaedic prosthetic component of claim 10, wherein the porous three-dimensional structure has a porosity that is between about 20% and about 95%.

12. The orthopaedic prosthetic component of claim 11, wherein the porous three-dimensional structure has a porosity that is between about 50% and about 75%.

13. The orthopaedic prosthetic component of claim 10, wherein the first structure is a rhombic dodecahedron.

14. The orthopaedic prosthetic component of claim 10, wherein the second structure is a trigonal trapezohedron.

15. The orthopaedic prosthetic component of claim 10, wherein the first struts define an average first strut length, and at least some of the first struts have respective lengths that are different than the average first strut length and within 50% to 150% of the average first strut length.

* * * * *